United States Patent
Sekowski et al.

(10) Patent No.: US 7,625,708 B1
(45) Date of Patent: *Dec. 1, 2009

(54) IMMUNOHISTOCHEMISTRY METHOD FOR INTACT PLUCKED HAIR FOLLICLES

(75) Inventors: Jennifer W. Sekowski, Forest Hill, MD (US); Amanda E. Chambers, Baltimore, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 424 days.

This patent is subject to a terminal disclaimer.

(21) Appl. No.: 11/449,180

(22) Filed: Jun. 7, 2006

Related U.S. Application Data

(60) Provisional application No. 60/688,752, filed on Jun. 8, 2005.

(51) Int. Cl.
*G01N 33/53* (2006.01)
(52) U.S. Cl. .................. 435/7.1; 435/7.91; 435/792; 436/518

(58) Field of Classification Search .............. 435/7.1
See application file for complete search history.

(56) References Cited

OTHER PUBLICATIONS

No reference is cited in the whole prosecution. No US patent and no non-patent literature is cited by Examiner.*

* cited by examiner

*Primary Examiner*—Jacob Cheu
(74) *Attorney, Agent, or Firm*—Ulysses John Biffoni

(57) ABSTRACT

The various embodiments provide method of using hair follicle bulbs as biodosimeters for the detection of chemical exposure. The methods described herein utilize intact, plucked hair follicle bulbs and can be used to monitor real-time or near real-time changes in the levels of specific follicular bulb biomarkers to determine exposure to toxicants. By utilizing the living, responsive cells in the plucked hair follicle bulb in an immunohistochemical (IHC) analysis, the various embodiments mitigate the risks of false positives associated with segmental hair analysis and avoid the more invasive collection required for serum and urinalysis.

31 Claims, No Drawings

IMMUNOHISTOCHEMISTRY METHOD FOR INTACT PLUCKED HAIR FOLLICLES

RELATED APPLICATIONS

This application claims priority to U.S. Provisional Patent Application Ser. No. 60/688,752, entitled "Immunohistochemistry Method for Intact, Plucked Hair Follicle," by Sekowski et al., and filed on Jun. 8, 2005, which is commonly assigned and incorporated by reference herein in its entirety. This application is further related to U.S. patent application Ser. No. 11/416,509, entitled "Hair Follicle Bulb as a Biodosimeter," by Sekowski et al., and filed Apr. 26, 2006, which is also commonly assigned.

GOVERNMENTAL INTEREST

The invention described herein may be manufactured, used and licensed by or for the U.S. Government.

FIELD OF THE INVENTION

The present invention relates generally to immunohistochemistry, and in particular the present invention relates to the use of a hair follicle bulb as a biodosimeter for chemical exposure.

BACKGROUND

The skin covering the human body is rich in hair and hair follicles, with over 90% of its surface supporting some type of hair. Biologically defined, hair is the epidermal tissue that is derived from the involutions, also called follicles, located in the skin. The bulb region of the hair follicle contains the metabolically active cells of the hair, which derive nutrients from the circulating blood. As such, hair follicle bulb cells are responsive in real-time or near real-time to toxic insults, in much the same way as skin cells.

Chemicals or heavy metals present in the body are brought into contact with the hair follicle by the circulating blood. There, they may enter the follicle and may potentially be incorporated into the hair shaft by the proliferating matrix cells found in the hair bulb. The ability to be incorporated into the hair shaft has led to the possibility of detecting exposure to chemicals and heavy metals via the hair shaft. Termed segmental hair analysis, this has become a popular method to determine exposure to drugs of abuse (e.g. cocaine, amphetamine, methamphetamine, heroin, marijuana, and steroids), therapeutic drugs (e.g. ephedrine, benzodiazepines, and barbiturates), and inorganic heavy metals (e.g. arsenic, lead, and mercury).

Recent reports suggest that long-term exposure to pesticides (e.g. carbamate, organochlorine, and organophosphate (OP)) can also be detected using segmental hair analysis. Others have demonstrated that methomyl, a carbamate pesticide, could be detected in the rabbit hair shaft following a 4-month daily methomyl exposure.

To carry out segmental hair analysis, scalp hair is cut into 1, 2, and 3 cm segments, which approximately corresponds to 1, 2, and 3 month's growth. If scalp hair is not available, other sources of hair can be used for analysis. Segmental analysis can be accomplished with as little as one hair or up to 200 mg of hair may be used to allow confirmation testing. The segments are typically washed to remove external contaminants and the chemicals in the hair are extracted by alkaline digestion, enzymatic treatment, or acid extraction. Several analytical methods are available to determine the concentration, if any, of a particular substance in the hair. Immunoassay, High Performance Liquid Chromatography (HPLC), Capillary Electrophoresis (CE), Gas Chromatography-Mass Spectrometry (GC-MS), tandem mass spectrometry (MS-MS) and Liquid Chromatography-Mass Spectrometry (LC-MS) can be used for analysis. Of these, the most superior in sensitivity, selectivity, and specificity is GC-MS separation and selective ion monitoring (SIM) quantitation. However, tandem MS can be used if the compound of interest is unstable in gas chromatograph separation/analysis.

The main advantage of segmental hair analysis is that successful analysis is possible even months after exposure. Other sample sources for testing, such as urine, offer an immediate window of testing, however, most drugs can only be detected 1 to 3 days following initial use. Although segmental hair analysis is becoming increasingly popular, the risk of a false positive is high when compared to urine or blood testing. Dark hair color, poor personal hygiene, and passive exposure can all lead to false positive segmental hair analysis results.

Due to the increased risk of false positives associated with segmental hair analysis and the more invasive collection required for serum and urinalysis, and for other reasons stated below that will become apparent to those skilled in the art upon reading and understanding the present specification, there is a need in the art for alternative methods of determining levels of toxicant exposure.

SUMMARY

The various embodiments include the detection of chemical exposure through the preparation of intact, plucked hair follicle bulbs. The methods described herein can be used to monitor real-time or near real-time changes in the levels of specific follicular bulb biomarkers to determine exposure to toxicants. By utilizing the living, responsive cells in the plucked hair follicle bulb in an immunohistochemical (IHC) analysis, the various embodiments mitigate the risks of false positives associated with segmental hair analysis and avoid the more invasive collection required for serum and urinalysis. The various embodiments of the invention rely upon detection of various chemical-responsive proteins (biomarkers) in intact, plucked hair follicle bulbs. Rather than measuring the toxicant or its metabolites, changes in specific toxicant-responsive follicle bulb proteins are monitored to determine toxicant exposure.

The invention further includes methods of varying scope.

DETAILED DESCRIPTION

In the following detailed description of the present embodiments, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that process, chemical or mechanical changes may be made without departing from the scope of the present invention. The following detailed description is, therefore, not to be taken in a limiting sense, and the scope of the present invention is defined only by the appended claims and equivalents thereof.

Carbamate, OP pesticides and OP nerve agents exert their effects through the inhibition of Acetylcholinesterase (AChE). Acetylcholinesterase is the enzyme responsible for the breakdown of the neurotransmitter acetylcholine (ACh). Following AChE inhibition, ACh accumulates in the synapses. As a result of the increased ACh concentration in the synapses, the portions of the sympathetic and parasympathetic nervous system that control smooth muscle, cardiac muscle and exocrine glandular function are overstimulated. Urine and blood tests are available to determine the presence of OP compound hydrolysis products. Although conclusive, most require derivatization prior to analysis. Currently, measurement of AChE levels in the blood is the fastest and most commonly employed method to determine exposure to pesticides and nerve agents. Although this test is faster than analyzing hydrolysis products in the urine or blood, there are still several drawbacks to the test due to the inherent nature of AChE. First, it has been reported that there is a 10-18% interindividual variation and a 3 to 7% intraindividual variation for AChE levels. Thus, without a known personal baseline, it is difficult to conclude if a person has been exposed to a nerve agent if they show inhibition levels of less than 20%. Secondly, due to the de novo synthesis of new AChE, this method cannot be used for retrospective determination of exposure. The various embodiments of the invention facilitate simple and rapid determination of exposure to carbamate and OP pesticides and OP nerve agents.

In order to reduce the invasiveness of blood or urine based tests, a new methodology using plucked hair follicle bulbs was developed by the present inventors. See, U.S. patent application Ser. No. 11/416,509, filed Apr. 26, 2006. Plucked hair follicle bulb collection is relatively non-invasive, can be performed in the field, and samples can be easily preserved, stored, and shipped. Additionally, enough hair sample can easily be collected and stored in order to repeat testing for further confirmation. By employing IHC, this method overcomes the false positives associated with traditional segmental hair analysis. By measuring the changes in specific biomarker levels in the living portion of the hair follicle bulb, the IHC technique employed in this method detects response to exposure in near real-time.

IHC successfully bridges the fields of immunology, chemistry and histology, resulting in a simple, yet powerful research and diagnostic tool. Antibodies are used to identify specific antigens within tissue sections. Following antigen-antibody binding, the antigen is then demonstrated in the tissue with a colored dye or fluorochrome. Because intact tissue is used, IHC can be used to determine the location of specific antigens.

Disclosed herein are modifications to classical IHC methodologies in order to study intact, plucked hair follicle bulbs. Unlike traditional segmental hair analysis in which the specific chemical or metabolites are extracted from the hair shaft and measured, the methods described herein can be used to monitor real-time or near real-time changes in the levels of specific follicular bulb biomarkers to determine exposure to toxicants.

By utilizing the living, responsive cells in the plucked hair follicle bulb in an IHC analysis, the various embodiments mitigate the risks of false positives associated with segmental hair analysis and avoid the more invasive collection required for serum and urinalysis. The various embodiments of the invention rely upon detection of various chemical-responsive proteins (biomarkers) in intact, plucked hair follicle bulbs using a novel immunohistochemistry (IHC) method. Rather than measuring the toxicant or its metabolites, changes in specific toxicant responsive follicle bulb proteins are monitored to determine toxicant exposure. Seventeen biomarkers were verified in U.S. patent application Ser. No. 11/416,509, Table 1 lists these biomarkers.

TABLE 1

Verified Biomarkers in the Rat Whisker Follicle Bulb

| Potential Biomarker | Function | Literature evidence (tissue type) |
|---|---|---|
| Actin | Cytoskeletal; cell vision | Rats exposed to sublethal dose of soman reported to have decreased levels of protein synthesis (brain) |
| Aldehyde Dehydrogenase (ALDH) | Metabolism; Phase II | Cells exposed to methylcholanthrene showed induction of ALDH (cell culture) |
| Androgen Receptor | Hormone Receptor | OP and OC pesticides were shown to act as antagonists of the AR |
| Brain derived neurotrophic factor (BDNF) | Neurotrophin | BDNF mRNA down-regulated in animals exposed to OP pesticides |
| CD 20 | Lymphocytes (B-lymphocytes) | Mice exposed to low-level sam showed slight increases of CD 19 (lungs) |
| Cytochrome P450 1A1 (CYP 1A1) | Metabolism; Phase I | Cells exposed to β-naphthaoflavone, phenobarbital and methylcholanthrene showed increase CYP1A1 activity (cell culture) |
| Estrogen Receptor α | Hormone Receptor | OP pesticide diazinon demonstrated estrogenic activity in ovarian carcinoma cells (cell culture) |
| Glial cell line-derived neurotrophic factor (GDNF) | Neurotrophic factor; cytokine family | GDNF mRNA expression increased in rats exposed to sub-chronic doses of phen-cyclidine (rat brain); also known to aid in repair following neuronal damage |
| Glucose Transporter 1 | Membrane bound; transport | Cells exposed to lipophilic pesticides showed a decrease in glucose transporter activity (cell culture) |
| Glutathion-S-Transferase (GST) | Metabolism; Phase II | Cells exposed to methylcholanthrene showed induction of GST (cell culture) |
| NAD(P)H: Quinone Oxidoreductase I (NQO I) | Metabolism; Phase II | Cells exposed to methylcholanthrene showed induction of NQO I (cell culture) |
| Sodium-Potassium ATPase β1 | Membrane bound; ion transport | Cells exposed to lipophilic pesticides showed a decrease in Na+/K+-ATPase activity (cell culture) |
| α-Tubulin | Cytoskeletal; cell division | Rats exposed to sublethal doses of soman had decreased levels of protein synthesis (brain) |
| β-Tubulin | Cytoskeletal; cell division | Rats exposed to sublethal doses of soman had decreased levels of protein synthesis (brain) |
| Tumor Necrosis Factor-α (TNF-α) | Cytokine | Rats exposed to low-level sarin shown increased mRNA for TNF-α (brain) |

Hair follicles cycle through three stages: growth (anagen), involution (catagen) and rest (telogen). A number of proteins cycle along with the hair follicle growth stages, thus the growth stage of individual hairs can be monitored by the presence or absence of these specific cycling proteins. Correct measurement of growth stage is extremely important for research involving hair follicles. Hair follicle bulbs must be in the same growth stage in order to compare levels of proteins that change in response to chemical exposure. The control proteins described in this work are Alkaline Phosphatase (AP) and Matrix Metalloproteinase-2 (MMP-2).

Alkaline Phosphatase (EC 3.1.3.1) (AP) is a zinc metalloenzyme with a wide range of cellular functions. There are four distinct forms of AP: Intestinal (IAP), Placental (PLAP), Placental-like (ALP-1) and Tissue Non-Specific (TNAP). The Tissue Non-Specific isoform of Alkaline Phosphatase was chosen for this work due to the fact that it is widely expressed in a number of tissues compared to the Intestinal, Placental and Placental-like isoforms, which are tissue specific. Since the 1940s, scientists have been studying the role of AP in hair growth. Increased interest in the role of AP in the hair follicle occurred when dermopathologists observed decreased or absent AP activity in early alopecia areata, an autoimmune response causing hair loss in patches.

The levels of AP have been studied in the Long-Evans hooded rat skin model. Slight levels of activity have been observed in early anagen. However, a marked increase has been observed in AP activity in late anagen, when rapid epithelial proliferation occurs. When the hair follicle is in telogen, AP activity is not observed. It has further been reported that human hair follicles show an absence of AP in the dermal papilla of telogen follicles. AP activity has been observed in all stages of hair growth in C57 BL-6 mouse skin. However, this data conflicts with the previous reports described above and there has been speculation that the observed differences might be due to strain specific differences.

Due to the conflicting reports on the presence of AP in the hair follicle only during growth stages, an additional growth control was used. Matrix Metalloproteinase-2 (EC 3.4.24.24) has been shown to play a key role in the remodeling and cell migration in the extracellular matrix and is strongly expressed in anagen hair follicles and weakly expressed in telogen follicles.

Most published reports using IHC to study the proteins in the hair follicle use sectioned skin biopsies. One manuscript was found to describe the use of unsectioned, plucked hair follicles in IHC, i.e., the study of DOPA-negative melanocytes. See, Horikawa, T. et al., DOPA-Negative Melanocytes in the Outer Root Sheath of Human Hair Follicles Express Premelanosomal Antigens But Not a Melanosomal Antigen or the Melanosome-Associated Glycoproteins Tyrosinase, TRP-1, and TRP-2. *The Journal of Investigative Dermatology* 1996, 106 (1), 28-35. Since the proteins of interest examined in this work are not found in the Outer Root Sheath (ORS), the methods of the various embodiments necessarily differ from the method described by Horikowa et al. By digesting the ORS, the internal structure of the hair follicle bulb can be examined without time-consuming sectioning.

Antibodies

The mouse monoclonal antibodies identified for use with various embodiments were: anti-Actin (Novus Biologicals, Littleton, Colo., USA), anti-Breast Cancer Antigen 1 (BRCA 1) (Santa Cruz Biotechnology, Santa Cruz, Calif., USA), anti-CD3 (Santa Cruz Biotechnology, Santa Cruz, Calif., USA), anti-Glial cell-line derived neurotrophic factor (GDNF) (Santa Cruz Biotechnology, Santa Cruz, Calif., USA), anti-Glutathion S-Transferase (GST) (Chemicon, Temecula, Calif., USA), anti-Keratin 10 (Neo Markers, Fremont, Calif., USA), anti-Na$^+$/K$^+$ATPase α1 (Santa Cruz Biotechnology, Santa Cruz, Calif., USA), and anti-Na$^+$/K$^+$ATPase β1 (Santa Cruz Biotechnology, Santa Cruz, Calif., USA).

The rabbit polyclonal antibodies identified for use with various embodiments were: anti-Androgen Receptor (AR) (Santa Cruz Biotechnology, Santa Cruz, Calif., USA), anti-Brain Derived Neutrophic Factor (BDNF) (Santa Cruz Biotechnology, Santa Cruz, Calif., USA), anti-Cytochrome P450 1A1 (CYP1A1) (Santa Cruz Biotechnology, Santa Cruz, Calif., USA), anti-CD20 (Santa Cruz Biotechnology, Santa Cruz, Calif., USA), anti-Estrogen Receptor α (ER α) (Santa Cruz Biotechnology, Santa Cruz, Calif., USA), anti-Glyceraldehyde Phosphate Dehydrogenase (GAPDH) (Novus Biologicals, Littleton, Colo., USA), anti-Glucose Transporter 1 (Glut 1) (Santa Cruz Biotechnology, Santa Cruz, Calif., USA) and anti-NAD(P)H: quinone oxidoreductase I (NQO 1) (Santa Cruz Biotechnology, Santa Cruz, Calif., USA).

The goat polyclonal antibodies identified for use with various embodiments were: anti-Aldehyde Dehydrogenase 1A2 (ALDH1A2) (Santa Cruz Biotechnology, Santa Cruz, Calif., USA), anti-Tissue Non-Specific Alkaline Phosphatase (TNAP) (Santa Cruz Biotechnology, Santa Cruz, Calif., USA) and anti-Tumor Necrosis Factor-α (TNF-α) (Santa Cruz Biotechnology, Santa Cruz, Calif., USA).

The chicken polyclonal antibody identified for use with various embodiments was: anti-Matrix Metalloproteinase-2 (MMP-2) (Abcam, Cambridge, Mass., USA).

The Cy5-labeled goat anti-rabbit IgG and Cy5-labeled goat anti-mouse IgG were purchased from Amersham Biosciences (Pisataway, N.J., USA). Cy5-labeled and Cy3-labeled rabbit anti-goat IgG was purchased from Chemicon (Temecula, Calif., USA). Alexa Fluor 532-labeled anti-Chicken IgY was made from rabbit anti-Chicken IgY (Abcam, Cambridge, Mass., USA) labeled with the Alexa Fluor 532 Protein Labeling Kit (Molecular Probes, Eugene, Oreg., USA). Alkaline phosphatase conjugated anti-rabbit IgG, anti-mouse IgG, anti-goat IgG and anti-chicken IgY were purchased from Santa Cruz Biotechnology (Santa Cruz, Calif., USA).

IMMUNOHISTOCHEMISTRY

Example #1

Hair samples were fixed briefly in fresh acetone, removed and incubated in PBS (0.1M Phosphate and 0.15M NaCl, pH 7) for 15 minutes at room temperature. Hairs were then mounted onto glass slides, leaving the bulb and lower shaft of the follicle free. The hairs were then digested with 0.1 mg/ml Proteinase K (Invitrogen, Carlsbad, Calif., USA) in 20 mM Tris-HCl, pH 7.5 containing 50 mM CaCl2 for 1 hour at 37° C. Following digestion, the entire slide was washed with TTBS 3 times, 5 minutes per wash. Each hair follicle was then covered with primary antibody (1:25-1:50). Slides were incubated at 4° C. overnight in a humidity chamber. Following incubation with the primary antibody, slides were washed with TTBS 3 times, 5 minutes per wash. Then each lower shaft and hair follicle was immersed in Cy5-labeled secondary antibody (1:200-1:500). Slides were maintained at 37° C. for 1 hour in darkness. Following secondary antibody incubation, slides were washed 3 times, 5 minutes per wash, with TTBS. For dual labeling, 10 μl of anti-TNAP (1:25) was used to cover each hair follicle. Slides were incubated in a humidity chamber at 37° C. for 1 hour. Following incubation with anti-TNAP, the slides were washed with TTBS 3 times, 5 minutes per wash. Hairs were then covered with Cy3 labeled rabbit anti-goat IgG (1:200) for 1 hour at 37° C. in a dark humidity chamber. Slides were then washed with TTBS 3 times, 5 minutes per wash, and rinsed with ddiH2O 3 times, 2 minutes per wash. Images of the stained hair follicle bulbs were analyzed on an Affymetrix 428 scanner (Affymetrix, Santa Clara, Calif., USA). Images of the stained hair follicle bulbs were analyzed using Affymetrix Jaguar 2.0 software (Affymetrix, Santa Clara, Calif., USA).

Example #2

Hair samples were fixed briefly in fresh acetone, removed and incubated in TBS (50 mM Tris, pH 8.0 containing 150 mM NaCl) at room temperature for 15 minutes. The hairs were mounted onto glass slides, leaving the bulb and lower shaft of the follicle free and digested with 0.1 mg/ml Proteinase K (Invitrogen, Carlsbad, Calif., USA) in 20 mM Tris-HCl, pH 7.5 containing 50 mM $CaCl_2$ at 37° C. for 1 hr. Following digestion, the entire slide was washed with TTBS 4 times, 5 min per wash. Individual hair follicle lower shaft and bulb were blocked at room temperature for 10 minutes with TTBS containing 5% BSA. The blocking solution was blotted off and each hair follicle lower shaft and bulb was covered with primary antibody (1:25-1:50) (see Table 2 for dilutions). Slides were incubated at 4° C. overnight in a humidity chamber. Following incubation with the primary antibody, slides were washed with TTBS 4 times, 5 min per wash. Each lower shaft and hair follicle bulb was immersed in Cy5-labeled secondary antibody (1:400). Slides were incubated at room temperature for 1 hr in darkness. Following secondary antibody incubation, slides were washed 4 times, 5 min per wash, with TTBS. For triple labeling, 10 µl of an anti-TNAP (1:25) and anti-MMP-2 (1:50) mixture was used to cover each hair follicle lower shaft and bulb. Slides were incubated in a dark humidity chamber at room temperature for 1 hr. Following incubation with the anti-TNAP/anti-MMP-2 mixture, the slides were washed with TTBS 4 times, 5 min per wash. Hairs were covered with a mixture Cy3-labeled rabbit anti-goat IgG (1:400) and Alexa 532 rabbit anti-chicken IgY (1:400) in a dark humidity chamber at room temperature for 1 hr. Slides were washed with TTBS 4 times, 5 min per wash, and rinsed with $diH_20$ 3 times, 2 min per wash. Images were analyzed on Affymetrix 428 scanner (Affymetrix, Santa Clara, Calif., USA) using Affymetrix Jaguar 2.0 software (Affymetrix, Santa Clara, Calif., USA).

CONCLUSION

Detection of chemical exposure through the preparation of intact, plucked hair follicle bulbs has been described herein. The methods described herein can be used to monitor real-time or near real-time changes in the levels of specific follicular bulb biomarkers to determine exposure to toxicants. By utilizing the living, responsive cells in the plucked hair follicle bulb in an immunohistochemical (IHC) analysis, the various embodiments mitigate the risks of false positives associated with segmental hair analysis and avoid the more invasive collection required for serum and urinalysis. The various embodiments of the invention rely upon detection of various chemical-responsive proteins (biomarkers) in intact, plucked hair follicle bulbs. Rather than measuring the toxicant or its metabolites, changes in specific toxicant-responsive follicle bulb proteins are monitored to determine toxicant exposure.

Although specific embodiments have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A method of detecting exposure of a subject to a chemical, comprising:
   collecting a hair sample having an intact hair follicle bulb from the subject;
   digesting an outer root sheath of the hair follicle bulb from the hair sample;
   blocking the hair follicle bulb;
   dual labeling the hair follicle bulb by:
     incubating the hair follicle bulb with a primary antibody to bind a first protein responsive to the chemical;
     demonstrating the bound first protein in the hair follicle bulb by incubating the hair follicle bulb with a first dye-labeled secondary antibody;
     incubating the hair follicle bulb with a positive control antibody to bind a second protein indicative of a growth stage of the hair follicle bulb; and
     demonstrating the bound second protein in the hair follicle bulb by contacting the hair follicle bulb with a second dye-labeled secondary antibody;
   detecting a change in level of the second protein from the hair follicle bulb as an indication of the growth stage of the hair follicle bulb; and
   detecting a change in level of the first protein from the hair follicle bulb as an indication of exposure to the chemical if the detected level of the second proteins is indicative of the hair follicle bulb being in a desired growth stage at a time of collecting the hair sample, and wherein the desired growth stage of the hair follicle bulb is an anagen growth stage.

2. The method of claim 1, wherein digesting each hair follicle bulb comprises digesting each hair follicle bulb with Proteinase K.

3. The method of claim 1, wherein the primary antibody is selected from the group consisting of mouse monoclonal antibodies, rabbit polyclonal antibodies and goat polyclonal antibodies.

4. The method of claim 3, wherein the mouse monoclonal antibodies are selected from the group consisting of anti-Actin, anti-Breast Cancer Antigen 1, anti-Glial cell-line derived neurotrophic factor, anti-Glutathion S-Transferase, and anti-Na+/K+ATPase β1.

5. The method of claim 3, wherein the rabbit polyclonal antibodies are selected from the group consisting of anti-Androgen Receptor, anti-Brain Derived Neutrophic Factor, anti-Cytochrome P450 1A1, anti-CD20, anti-Estrogen Receptor α, anti-Glyceraldehyde Phosphate Dehydrogenase, anti-Glucose Transporter 1, and anti-NAD(P)H: quinone oxidoreductase I.

6. The method of claim 3, wherein the goat polyclonal antibodies are selected from the group consisting of anti-Aldehyde Dehydrogenase 1A2 and anti-Tumor Necrosis Factor-α.

7. The method of claim 1, wherein the first dye-labeled secondary antibody is a Cy5-labeled secondary antibody and wherein the second dye-labeled secondary antibody is a Cy3-labeled secondary antibody.

8. The method of claim 7, wherein the first dye-labeled secondary antibody is selected from the group consisting of Cy5-labeled goat anti-rabbit IgG, Cy5-labeled goat anti-mouse IgG, and Cy5-labeled rabbit anti-goat IgG, and wherein the second dye-labeled secondary antibody is Cy3-labeled rabbit anti-goat IgG.

9. The method of claim 1, wherein the first protein responsive to the chemical is selected from the group consisting of Actin, Aldehyde Dehydrogenase, Androgen Receptor, Brain-derived neurotrophic factor, CD 20, Cytochrome P450 1A1, Estrogen Receptor α, Glial cell line-derived neurotrophic factor, Glucose Transporter 1, Glutathion-S-Transferase, NAD(P)H: Quinone Oxidoreductase I, Sodium-Potassium ATPase β1, α-Tubulin, β-Tubulin, and Tumor Necrosis Factor-α.

10. The method of claim 1, wherein the chemical is selected from the group consisting of Carbamate, Organophosphorus (OP) pesticides, Organophosphorus (OP) nerve agents, methylphosphonothioc acid S-[2-[bis(1-methylethyl)

amino]ethyl] O-ethyl ester (VX), Hexahydro- 1.3,5-trinitro-1,3,5-triazine (RDX) and Octahydro-1,3,5,7-tetranitro-1,3,5,7 tetrazine (HMX).

11. The method of claim 10, wherein the chemical is Hexahydro- 1,3,5-trinitro-1,3,5-triazine (RDX) and the chemical-responsive protein is selected from the group consisting of Androgen Receptor, Cytochrome P450 1A1, Estrogen Receptor α, Glial cell line-derived neurotrophic factor, Glucose Transporter 1, and Glutathion-S-Transferase.

12. The method of claim 1, wherein the positive control antibody is selected from the group consisting of anti-Tissue Non-Specific Alkaline Phosphatase (TNAP), Matrix Metalloproteinase-2 (MMP-2) and combination thereof.

13. A method of detecting exposure of a subject to a chemical, comprising:
    collecting a hair sample having an intact hair follicle bulb from the subject;
    digesting an outer root sheath of the hair follicle bulb from the hair sample;
    blocking the hair follicle bulb;
    triple labeling the hair follicle bulb by:
        incubating the hair follicle bulb with a primary antibody to bind a first protein responsive to the chemical;
        demonstrating the bound first protein in the hair follicle bulb by incubating the hair follicle bulb with a first dye-labeled secondary antibody,
        incubating the hair follicle bulb with positive control antibodies to bind a second and a third protein indicative of a growth stage of the hair follicle bulb; and
        demonstrating the bound second and third proteins in the hair follicle bulb by contacting the hair follicle bulb with a second dye-labeled secondary antibody and a third dye-labeled secondary antibody;
    detecting a change in level of the second and third proteins from the hair follicle bulb as an indication of the growth stage of the hair follicle bulb; and
    detecting a change in level of the first protein from the hair follicle bulb as an indication of exposure to the chemical if the detected level of the second and third proteins are indicative of the hair follicle bulb being in a desired growth stage at a time of collecting the hair sample, and wherein the desired growth stage of the hair follicle bulb is an anagen growth stage.

14. The method of claim 13, wherein digesting each hair follicle bulb comprises digesting each hair follicle bulb with Proteinase K.

15. The method of claim 13, wherein the primary antibody is selected from the group consisting of mouse monoclonal antibodies, rabbit polyclonal antibodies and goat polyclonal antibodies.

16. The method of claim 15, wherein the mouse monoclonal antibodies are selected from the group consisting of anti-Actin, anti-Breast Cancer Antigen 1, anti-Glial cell-line derived neurotrophic factor, anti-Glutathion S-Transferase, and anti-Na+/K+ATPase β1.

17. The method of claim 15, wherein the rabbit polyclonal antibodies are selected from the group consisting of anti-Androgen Receptor, anti-Brain Derived Neutrophic Factor, anti-Cytochrome P450 1A1, anti-CD20, anti-Estrogen Receptor α, anti-Glyceraldehyde Phosphate Dehydrogenase, anti-Glucose Transporter 1, and anti-NAD(P)H: quinone oxidoreductase I.

18. The method of claim 15, wherein the goat polyclonal antibodies are selected from the group consisting of anti-Aldehyde Dehydrogenase 1 A2 and anti-Tumor Necrosis Factor-α.

19. The method of claim 13, wherein the first dye-labeled secondary antibody is a Cy5-labeled secondary antibody, wherein the second dye-labeled secondary antibody is a Cy3-labeled secondary antibody, and wherein the third dye-labeled secondary antibody is an AlexaFluor532-labeled secondary antibody.

20. The method of claim 19, wherein the first dye-labeled secondary antibody is selected from the group consisting of Cy5-labeled goat anti-rabbit IgG, Cy5-labeled goat anti-mouse IgG, and Cy5-labeled rabbit anti-goat IgG, and wherein the second and third dye-labeled secondary antibodies are Cy3-labeled rabbit anti-goat IgG and AlexaFluor532-labeled rabbit anti-chicken IgY.

21. The method of claim 13, wherein the first protein responsive to the chemical is selected from the group consisting of Actin, Aldehyde Dehydrogenase, Androgen Receptor, Brain-derived neurotrophic factor, CD 20, Cytochrome P450 1A1, Estrogen Receptor α, Glial cell line-derived neurotrophic factor, Glucose Transporter 1, Glutathion-S-Transferase, NAD(P)H: Quinone Oxidoreductase I, Sodium-Potassium ATPase β1, α-Tubulin, β-Tubulin, and Tumor Necrosis Factor-α.

22. The method of claim 13, wherein the chemical is selected from the group consisting of Carbamate, Organophosphorus (OP) pesticides, Organophosphorus (OP) nerve agents, methylphosphonothioc acid S-[2-[bis(1-methylethyl) amino]ethyl] O-ethyl ester (VX), Hexahydro-1,3,5-trinitro-1,3,5-triazine (RDX) and Octahydro-1,3,5,7-tetranitro-1,3,5,7 tetrazine (HMX).

23. The method of claim 22, wherein the chemical is Hexahydro-1,3,5-trinitro-1,3,5-triazine (RDX) and the chemical-responsive protein is selected from the group consisting of Androgen Receptor, Cytochrome P450 1 A1, Estrogen Receptor α, Glial cell line-derived neurotrophic factor, Glucose Transporter 1, and Glutathion-S-Transferase.

24. The method of claim 13, wherein the positive control antibodies are anti-Tissue Non-Specific Alkaline Phosphatase (TNAP) and Matrix Metalloproteinase-2 (MMP-2).

25. A method of detecting exposure of a subject to a chemical, comprising:
    collecting a hair sample having an intact hair follicle bulb from the subject;
    digesting an outer root sheath of the hair follicle bulb with Proteinase K;
    blocking the hair follicle bulb;
    triple labeling the hair follicle bulb by:
        incubating the hair follicle bulb with a primary antibody to bind a first protein responsive to the chemical;
        demonstrating the bound first protein in the hair follicle bulb by incubating the hair follicle bulb with a first dye-labeled secondary antibody;
        incubating the hair follicle bulb with anti-Tissue Non-Specific Alkaline Phosphatase (TNAP) antibody to bind TNAP and anti-Matrix Metalloproteinase-2 (MMP-2) antibody to bind MMP-2; and
        demonstrating the bound TNAP and MMP-2 in the hair follicle bulb by contacting the hair follicle bulb with a second dye-labeled secondary antibody and a third dye-labeled secondary antibody, respectively;
    detecting a change in level of the bound TNAP and MMP-2; and
    detecting a change in level of the first protein from the hair follicle bulb as an indication of exposure to the chemical if the detected levels of the bound TNAP and MMP-2 are indicative of the hair follicle bulb being in an anagen growth stage at a time of collecting the hair sample.

26. The method of claim 25, wherein the first dye-labeled secondary antibody is a Cy5-labeled secondary antibody and wherein the second and third dye-labeled secondary antibodies are a Cy3-labeled secondary antibody and an AlexaFluor532-labeled secondary antibody.

27. The method of claim 25, wherein the primary antibody is selected from the group consisting of mouse monoclonal antibodies, rabbit polyclonal antibodies and goat polyclonal antibodies.

28. The method of claim 25, wherein the first protein responsive to the chemical is selected from the group consisting of Actin, Aldehyde Dehydrogenase, Androgen Receptor, Brain-derived neurotrophic factor, CD 20, Cytochrome P450 1 A1, Estrogen Receptor α, Glial cell line-derived neurotrophic factor, Glucose Transporter 1, Glutathion-S-Transferase, NAD(P)H: Quinone Oxidoreductase I, Sodium-Potassium ATPase β1, α-Tubulin, β-Tubulin, and Tumor Necrosis Factor-α.

29. The method of claim 28, wherein the first dye-labeled secondary antibody is selected from the group consisting of Cy5-labeled goat anti-rabbit IgG, Cy5-labeled goat anti-mouse IgG, and Cy5-labeled rabbit anti-goat IgG, and wherein the second and third dye-labeled secondary antibodies are Cy3-labeled rabbit anti-goat IgG and AlexaFluor532-labeled rabbit anti-chicken IgY.

30. The method of claim 25, wherein the chemical is selected from the group consisting of Carbamate, Organophosphorus (OP) pesticides, Organophosphorus (OP) nerve agents, methylphosphonothioc acid S-[2-[bis(1-methylethyl)amino]ethyl] O-ethyl ester (VX), Hexahydro-1,3,5-trinitro-1,3,5-triazine (RDX) and Octahydro-1,3,5,7-tetranitro-1,3,5,7 tetrazine (HMX).

31. The method of claim 30, wherein the chemical is Hexahydro-1,3,5-trinitro-1,3,5-triazine (RDX) and the chemical-responsive protein is selected from the group consisting of Androgen Receptor, Cytochrome P450 1A1, Estrogen Receptor α, Glial cell line-derived neurotrophic factor, Glucose Transporter 1, and Glutathion-S-Transferase.

* * * * *